(12) United States Patent
Wang

(10) Patent No.: US 11,202,869 B2
(45) Date of Patent: Dec. 21, 2021

(54) AUTO-RETRACTABLE SAFETY BLOOD COLLECTION NEEDLE

(71) Applicant: Zuyang Wang, Shanghai (CN)

(72) Inventor: Zuyang Wang, Shanghai (CN)

(*) Notice: Subject to any disclaimer, the term of this patent is extended or adjusted under 35 U.S.C. 154(b) by 0 days.

(21) Appl. No.: 16/708,065

(22) Filed: Dec. 9, 2019

(65) Prior Publication Data

US 2020/0114089 A1    Apr. 16, 2020

Related U.S. Application Data

(63) Continuation of application No. PCT/CN2018/090525, filed on Jun. 8, 2018.

(30) Foreign Application Priority Data

Jun. 9, 2017 (CN) .......................... 201710433613.8

(51) Int. Cl.
*A61M 5/32* (2006.01)
*A61M 5/158* (2006.01)
*A61M 5/31* (2006.01)
*A61M 5/20* (2006.01)

(52) U.S. Cl.
CPC .......... *A61M 5/3234* (2013.01); *A61M 5/158* (2013.01); *A61M 5/3148* (2013.01); *A61M 5/3245* (2013.01); *A61M 2005/1586* (2013.01); *A61M 2005/2073* (2013.01); *A61M 2005/3247* (2013.01)

(58) Field of Classification Search
CPC .. A61M 5/3234; A61M 5/158; A61M 5/3148; A61M 5/3245; A61M 2005/1586; A61M 2005/2073; A61M 2005/3247; A61M 25/0637; A61M 25/0631; A61M 5/321; A61M 5/322; A61M 5/3243; A61B 5/15003; A61B 5/15074; A61B 5/153; A61B 5/150496; A61B 5/150519; A61B 5/150534; A61B 5/150633; A61B 5/150916; A61B 5/15; A61B 5/150564
See application file for complete search history.

(56) References Cited

FOREIGN PATENT DOCUMENTS

| CN | 102149420 A | 8/2011 |
|---|---|---|
| CN | 103892846 A | 7/2014 |
| CN | 106474592 A | 3/2017 |
| CN | 107281586 A | 10/2017 |
| JP | 2017038850 A | * 2/2017 |

* cited by examiner

*Primary Examiner* — Bhisma Mehta
*Assistant Examiner* — Neeraja Gollamudi
(74) *Attorney, Agent, or Firm* — Wayne IP LLC

(57) ABSTRACT

An auto-retractable blood collection needle, including: a needle holder including a first tube, a second tube and a holder tail; a needle installed in the first tube; a built-in sliding sleeve which is elongated and through and has a C-shaped cross section; a needle shield which is hollow and elongated; and a spring sheathed on the first tube. The second tube is installed in the built-in sliding sleeve and is capable of sliding back and forth. The built-in sliding sleeve is installed in the needle shield and is capable of sliding back and forth. A locking mechanism is formed by the holder tail and the needle shield. When the holder tail is unlocked from the needle shield, a force of the spring pushes the second tube to slide backward, and then the built-in sliding sleeve is driven to slide rearward to lock with the needle shield.

16 Claims, 14 Drawing Sheets

AUTO-RETRACTABLE SAFETY BLOOD COLLECTION NEEDLE

CROSS-REFERENCE TO RELATED APPLICATIONS

This application is a continuation of International Application No. PCT/CN2018/090525 with a filling date of Jun. 8, 2018, designating the United states, and further claims to the benefit of priority from Chinese Application No. 201710433613.8 with a filing date of Jun. 9, 2017. The content of the aforementioned applications, including any intervening amendments thereto, are incorporated herein by reference.

TECHNICAL FIELD

This application relates to medical instruments, and more particularly to an auto-retractable blood collection needle.

BACKGROUND OF THE INVENTION

Currently, safety blood collection needles that are effectively used in the market are mainly produced by American Becton, Dickinson and Company (BD) and German B. Braun Melsungen AG. For example, the American BD has produced an auto-retractable safety blood collection needle, and the principle thereof is described as follows. A spring and a locking device are installed at the front of the blood collection needle; the locking device is pressed after the blood collection is finished, and the needle is retracted into a needle sleeve by the spring to avoid needle stick injuries and cross infections.

However, the safety blood collection needles of American BD has the many defects in design, for example, the needle has a large size (a length of about 40 mm), leading to inconvenient use; a large distance between the needle and the needle holder causes a large inclination angle between the needle and the skin or vessel, so during operating, the vessels of patients are easy to be damaged. The button for releasing the spring is easy to be accidentally triggered. Moreover, the needle has the disadvantages of a complex structure and high cost, so the market demand cannot be met, and such safety blood collection needle is difficult to be popularized.

Key technical requirements for the safety blood collection needle are as follows.

1) A vertical distance between the needle and the bottom of the needle holder cannot exceed 1.5 mm, otherwise a large oblique angle is formed between the needle and the needle holder, indicating that the blood vessel is easy to be punctured by the needle tip.

2) The blood collection needle is required to be fixed at hand backs of patients for a long time, and thus it is required to be small in size, otherwise it is inconvenient touse and discomforts will be caused to the patients.

When adopting the widely commercially used blood collection needles, operators pull out the needle by holding the handle, and during the operation, the needle is rotated in the vessel, so the vessel has a potential risk of being damaged by the needle tip, which is the reason why patients with frequent infusions are prone to phlebitis. On the other hand, used needles are exposed, which easily causes needle stick injuries and secondary injuries, leading to the risk of cross infections.

In summary, the hose-type blood collection needle of the BD is inconvenient to use. Moreover, there is a potential risk of the secondary injuries, and vessels of patients may be damaged during the pulling out of the needle.

Other novel safety blood collection needles have the following technical problems. These blood collection needles cannot achieve a miniaturized design and convenient use while meeting the technical and safety requirements. Some products are well designed to overcome above technical problems, but batch production thereof cannot be realized.

SUMMARY OF THE INVENTION

In order to overcome above problems, the present invention has the following purposes.

1. Prevention of needle stick injuries and cross infections
   a) Potential damages to vessels of patients are reduced to a maximum extent in the infusion process.
   b) Medical staff are prevented from suffering potential needle stick injuries and cross infections to a maximum extent during the operation.
   c) Potential secondary damages and environmental pollution are prevented during the medical waste treatment.
2. Miniaturizing of product designs
3. Simplification of production process
   a) The product has a compact and simple design and a simple production process, thereby easily realizing the batch production.
   b) The cost is reduced while greatly improving quality and safety of the product.

In order to achieve above purposes, the present invention provides an auto-retractable blood collection needle, comprising:

a needle holder comprising a first tube, a second tube and a holder tail connected in sequence;
a needle;
a built-in sliding sleeve which is elongated and through and has a C-shaped cross section;
a needle shield which is hollow and elongated; and
a spring;

wherein a diameter of the second tube is larger than a diameter of the first tube; a rear of the needle is mounted in the first tube; the first tube and the second tube both are installed in the built-in sliding sleeve, and a built-in slider is provided on a peripheral surface of the second tube, and the second tube matches with the built-in slider to allow the second tube to slide back and forth; a holder tail of the needle holder is located outside a rear of the built-in sliding sleeve which is mounted in the needle shield and is capable of sliding back and forth; the holder tail is allowed to be locked at or unlocked from a rear of the needle shield; the spring is sheathed on the first tube; a front end of the spring abuts against an inner wall of the needle shield, and a rear of the spring abuts against a front end of the second tube;

a first locking mechanism is provided between the needle holder and the built-in sliding sleeve and is configured for locking the second tube with the built-in sliding sleeve; a second locking mechanism is provided between the built-in sliding sleeve and the needle shield and is configured for locking the built-in sliding sleeve with the needle shield; a third locking mechanism is provided between the holder tail and the needle shield and is configured for locking the holder tail with the needle shield;

when the holder tail is locked at a rear of the needle shield, the spring is in a compressed state, and a front end and a rear of the built-in sliding sleeve are respectively limited by the inner wall of the needle shield and the holder tail; when the holder tail is unlocked from the rear of the needle shield, the spring forces the second tube to slide rearward to a locking position of the first locking mechanism, so that the second tube is locked at the built-in sliding sleeve; the needle holder keeps sliding backward, and the built-in sliding sleeve is driven to slide rearward to a locking position of the second locking mechanism, so that the built-in sliding sleeve is locked at the needle shield; at this time, the needle is fully covered by the needle shield, and a needle tip is not exposed.

Further, the first locking mechanism comprises a first positioning part arranged on an outer wall of the second tube and a first locking part arranged on an inner wall of the built-in sliding sleeve; when the second tube slides to the locking position of the built-in sliding sleeve, the first positioning part is locked by the first locking part, so that the second tube is prevented from sliding out of the built-in sliding sleeve.

In some embodiments, the first positioning part comprises the built-in slider; the first locking part comprises a groove arranged along an axial direction of the built-in sliding sleeve and a first elastic arm arranged at a rear section of the groove; the built-in slider is limited to slide along a length of the groove; when the built-in slider slides along the groove to a rear end of the groove, the built-in slider pushes the first elastic arm to generate an elastic deformation to allow the built-in slider to pass; when the built-in slider reaches the rear end of the groove, the first elastic arm recovers from the elastic deformation, so that the built-in slider is locked and is prevented from sliding reversely.

In some embodiments, the first positioning part further comprises two side sliders which are symmetrically arranged on both sides of the built-in slider; the first locking part further comprises two first chutes which are arranged along the axial direction of the built-in sliding sleeve and are symmetrically arranged on two inner sides of the built-in sliding sleeve; the two side sliders are limited to slide along lengths of the two first chutes, respectively, so that the two side sliders are prevented from sliding out of the built-in sliding sleeve in a radial direction.

Further, the second locking mechanism comprises a second positioning part which is arranged on the built-in sliding sleeve and a second locking part which is provided on the inner wall of the needle shield; when the built-in sliding sleeve slides to the locking position of the second locking part, the second positioning part is locked by the second locking part, so that the built-in sliding sleeve is prevented from sliding out of the needle shield.

In some embodiments, the second positioning part comprises two protrusions respectively arranged on two axial sections of the built-in sliding sleeve; the second locking part comprises two second chutes and two second elastic arms which are respectively arranged at rear sections of the two second chutes, and the two protrusions are respectively limited to slide along lengths of the two second chutes; when the two protrusions slide towards rear ends of the two second chutes along the two second chutes, respectively, the two second elastic arms are pushed by the two protrusions to generate an elastic deformation to allow the two protrusions to pass; when the two protrusions respectively reach the rear ends of the two second chutes, the two second elastic arms recover from the elastic deformation, so that the two protrusions are locked and are prevented from sliding reversely.

Further, the third locking mechanism comprises a third positioning part arranged on the holder tail and a third locking part arranged on the rear of the needle shield; when the third positioning part is locked at the third locking part, the holder tail is locked at the rear of the needle shield, and the spring is in a compressed state; when the third positioning part is unlocked from the third locking part, a force of the spring pushes the second tube to allow the needle holder to move rearward.

In some embodiments, the third positioning part comprises two claws which are symmetrically arranged on a rear end surface of the holder tail and perpendicular to a central axis of the second tube; the third locking part comprises a first sheet-like portion and two bar-type holes; the first sheet-like portion extends from the rear of the needle shield along the axial direction of the needle shield, and is elastically movable in a radial direction; the two bar-type holes are symmetrically provided on the first sheet-like portion; the first sheet-like portion is operated to respectively insert the two claws into the two bar-type holes, or unlock the two claws from the two bar-type holes.

In some embodiments, the third positioning part comprises a first pressing portion and a first protrusion; the first pressing portion extends from a rear of the holder tail along an axial direction and is pressed along a radial direction; the first protrusion is provided on an outer wall of the first pressing portion; the third locking part comprises two second sheet-like portions and a first engaging portion; the two second sheet-like portions extend from the rear of the needle shield along the axial direction of the needle shield and are adjacent to each other, and the first engaging portion is arranged on one of the two second sheet-like portions; the first pressing portion is pressed to insert the first protrusion into the first engaging portion, or unlock the first protrusion from the first engaging portion.

In some embodiments, the third positioning part comprises two second protrusions which are respectively arranged on both sides of the holder tail; the third locking part comprises two second pressing portions and two second engaging portions; the two second pressing portions respectively extend rearward from two sides of the rear of the needle shield, and the two second pressing portions are pressed towards each other; the two second engaging portions are respectively provided on the two second pressing portions; when the two second pressing portions are respectively inserted in the two second engaging portions, the holder tail is locked at the rear of the needle shield; and when the second pressing portions on two sides of the rear of the needle shield are pressed towards each other, the two second protrusions are unlocked from the two second engaging portions, respectively.

Further, a maximum vertical distance between the needle and an outer wall of the lower shield is less than or approximately equal to 1.5 mm, so that a large oblique angle between the needle and the needle holder is avoided, and the vessels are not easily punctured by the needle tip. The separated design of the upper and lower shield allows the maximum vertical distance between the needle and the peripheral surface of the lower shield to be less than or approximately equal to 1.5 mm.

Further, a central axis of the first tube is parallel to a central axis of the second tube, and the central axis of the first tube is located between the central axis of the second tube and the inner wall of the lower shield, which can further reduce the maximum vertical distance between the needle and the outer wall of the lower shield.

Further, the blood collection needle further comprises a wing assembly which is sheathed on the needle shield; the wing assembly has two wings which are symmetrically arranged and overlap with each other after folded.

In some embodiments, the rear of the needle shield extends rearward to form a handheld portion; the handheld portion and the holder tail both are U-shaped and open rearward; a front section of the holder tail is located inside and locked with the handheld portion; a rear section of the holder tail is located behind a rear of the handheld portion; the third positioning part comprises two third pressing portions and two third protrusions; the two third pressing portions are two side walls of the rear section of the holder tail, respectively; the third locking part comprises two third engaging portions which are respectively provided on two side walls of the handheld portion; when the two third protrusions respectively engage with the two third engaging portions, the two third pressing portions are respectively located behind rears of two side walls of the handheld portion; and when the two third pressing portions located at two sides of the rear of the holder tail are pressed towards each other, the two third protrusions are respectively unlocked from the two third engaging portions.

Further, the first tube and the second tube are coaxially arranged.

Further, the needle shield is formed by fastening an upper shield and a lower shield together; the built-in sliding sleeve is installed in the upper shield; and two axial sections of the built-in sliding sleeve is attached on an inner wall of the lower shield.

The present invention adopts a specially designed needle holder, and the locking positions and protrusions which are located at middle and rear sections of the needle holder are engaged with each other to realize the locking or sliding of the needle shield and the built-in sliding sleeve between the needle and the needle shield. The automatic retraction of the needle holder or needle is realized by the spring which is mounted at the front section of the needle holder.

The auto-retractable safety blood collection needle is assembled with the following steps.

1) The needle is mounted at the front end of the first tube of the needle holder.
2) The second tube of the needle holder is inserted into the built-in sliding sleeve, and the holder tail is located outside the rear of the built-in sliding sleeve.
3) The spring is sheathed on the first tube.
4) The assembled built-in sliding sleeve, the needle holder and the spring are placed into the upper shield. The front end of the spring abuts against the stepped surface of the inner wall of the needle shield, and the rear of the spring abuts against the front end surface of the second tube.
5) The lower shield and the upper shield are fastened together to form the needle shield. At this time, the third locking part at the rear of the needle shield is locked with the third positioning part of the holder tail to lock the holder tail to the rear of the needle shield, and the built-in sliding sleeve is locked by the holder tail of the needle holder.
6) The wing assembly is sheathed on the peripheral surface of the needle shield.

The present invention mainly has the following advantages.

1. Prevention of needle stick injuries and cross infections
a) Potential damages to vessels of patients are reduced to a maximum extent in the infusion process.
b) Medical staff are prevented from suffering potential needle stick injuries and cross infections to a maximum extent during the operation.
c) Potential secondary damages and environmental pollution are prevented during the medical waste treatment.
2. Miniaturizing of product designs
3. Simplification of production process
a) The product has a compact and simple design and a simple production process, thereby easily realizing the batch production.
b) The cost is reduced while greatly improving quality and safety of the product.

Figure 1:
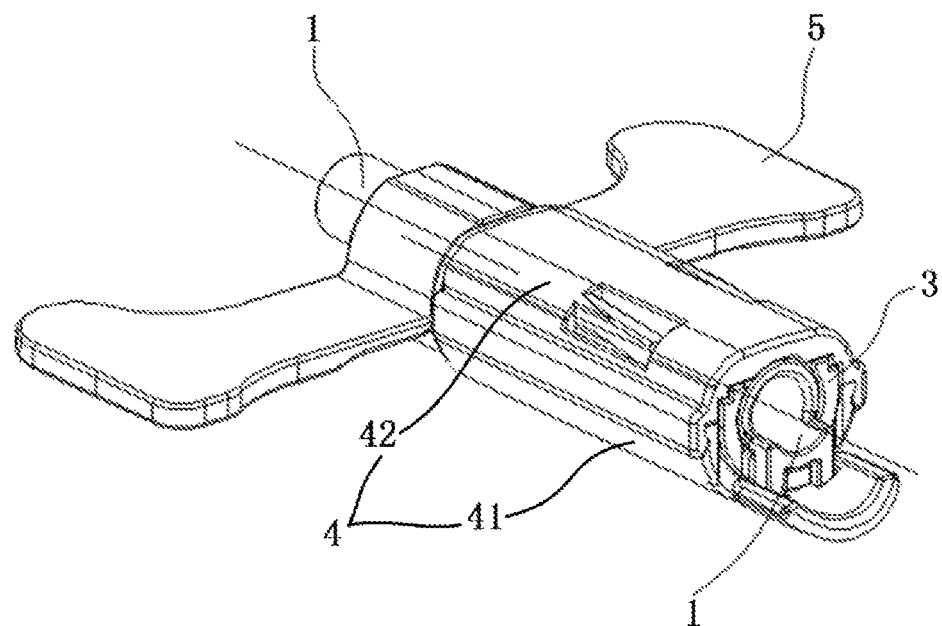
FIG. 1 is a schematic diagram of an auto-retractable blood collection needle according to a first embodiment of the present invention.

Reference numerals: 1, needle holder; 11, first tube; 12, second tube; 13, holder tail; 131, claw; 132, first pressing portion; 133, first protrusion; 134, second protrusion; 135, third pressing portion; 136, third protrusion; 14, bush; 15, built-in slider; 16, side slider; 2, needle; 21, needle tip; 3, built-in sliding sleeve; 31, groove; 311, rear groove; 312, fishhook-shaped through hole; 32, first elastic arm; 33, first chute; 34, protrusion; 35, bayonet; 36, axial section; 4, needle shield; 41, upper shield; 411, third tube; 412, fourth tube; 413, recess; 414, first sheet-like portion; 415, bar-type hole; 416, second sheet-like portion; 417, first engaging portion; 418, second pressing portion; 419, second engaging portion; 4110, handheld portion; 4111, third engaging portion; 4112, circular groove; 42, lower shield; 421, second chute; 422, second elastic arm; 423, circular protrusion; 5, wing assembly; 6, sheath; 7, additional needle; 8, spring; 91, first locking mechanism; 911, first positioning part; 912, first locking part; 92, second locking mechanism; 922, second locking part; 93, third locking mechanism; 931, third positioning part; 932, third locking part.

DETAILED DESCRIPTION OF EMBODIMENTS

Some preferred embodiments of the present invention will be described below with reference to the accompanying drawings, from which technical solutions of the present invention will be clearer for those skilled in the art. The present invention may be implemented by different embodiments, and embodiments and accompanying drawings herein are illustrative and are not intended to limit the scope of the present invention. In the drawings, components having the same structure are marked with the same numerals.

Example 1

Figure 2:
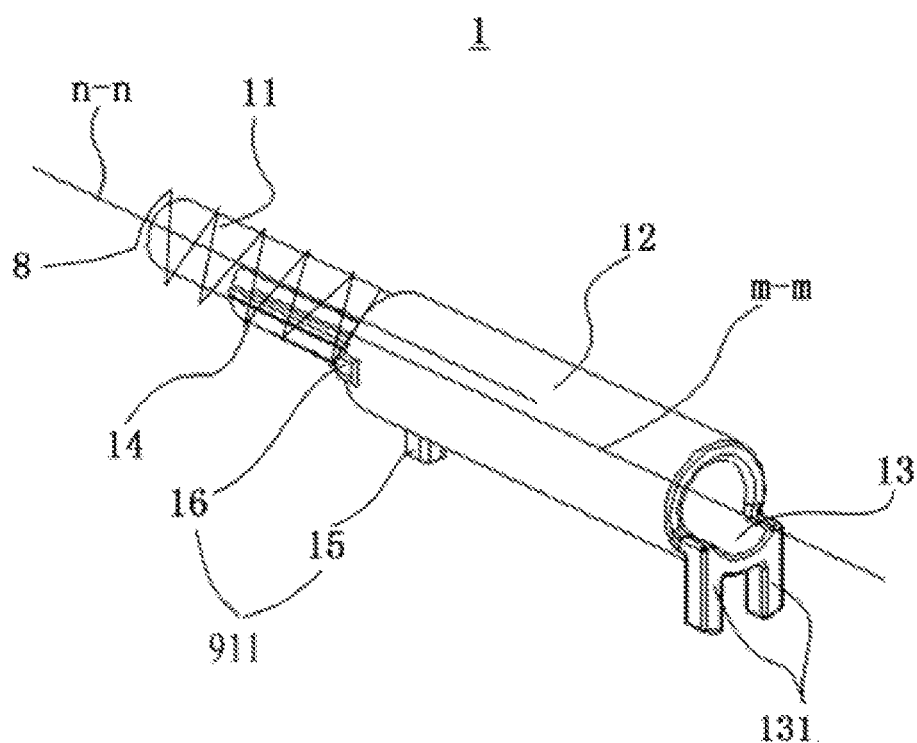
FIG. 2 is a schematic diagram of a needle holder according to the first embodiment of the present invention.

As shown in FIGS. 1-2, illustrated is an auto-retractable blood collection needle, comprising a needle holder 1, a needle 2 (not shown in FIGS. 1-2), a built-in sliding sleeve 3 and a needle shield 4 and a spring 8. The needle holder 1 comprises a first tube 11, a second tube 12 and a holder tail 13 connected in sequence, and a diameter of the second tube 12 is larger than a diameter of the first tube 11. A front end of the needle holder 2 extends forward from the needle holder, and a rear of the needle holder 2 is mounted in the first tube 11. The built-in sliding sleeve 3 is an elongate through block, and a cross section thereof is C-shaped. The first tube 11 and the second tube 12 both are installed in the built-in sliding sleeve 3; a built-in slider 15 is provided on a peripheral surface of the second tube 12, and the second tube 12 matches with the built-in slider 15 to allow the second tube to slide back and forth. The holder tail 13 is located outside a rear of the built-in sliding sleeve 3. The built-in sliding sleeve 3 is mounted in the needle shield 4 and is capable of sliding back and force, and the holder tail 13 can be locked at or unlocked from a rear of the needle shield 4. The spring 8 is sheathed on the first tube 11, where a front end of the spring 8 abuts against an inner wall of the needle shield 4, and a rear of the spring 8 abuts against a front end of the second tube 12. A first locking mechanism 91 is provided between the needle holder 1 and the built-in sliding sleeve 3 and is configured for locking the second tube 12. A second locking mechanism 92 is provided between the built-in sliding sleeve 3 and the needle shield 4 and is configured for locking the built-in sliding sleeve 3. A third locking mechanism 93 is provided between the holder tail 13 and the needle shield 4 and is configured for locking the holder tail 13.

When the holder tail 13 is locked to the rear of the needle shield 4, the spring 8 is in a compressed state, and the front end and rear of the built-in sliding sleeve 3 are respectively limited by the inner wall of the needle shield 4 and the holder tail 13. When the holder tail 13 is unlocked from the rear of the needle shield 4, the spring 8 forces the second tube 12 to slide backward to a locking position of the first locking mechanism 91, so that the second tube 12 is locked at the built-in sliding sleeve 3; the needle holder keeps sliding backward to drive the built-in sliding sleeve 3 to slide rearward to a locking position of the second locking mechanism 92, so that the built-in sliding sleeve 3 is locked at the needle shield 4. At this time, the needle 2 is fully covered by the needle shield 4, and a needle tip 21 is not exposed.

As shown in FIG. 2, a central axis n-n of the first tube 11 is parallel to a central axis m-m of the second tube 12. A bush 14 having a set length is provided on a part of the second tube 12, and the bush 14 covers only a part of a peripheral surface of the first tube 11. The spring 8 is provided on a peripheral surface of the bush 14.

Figure 3:
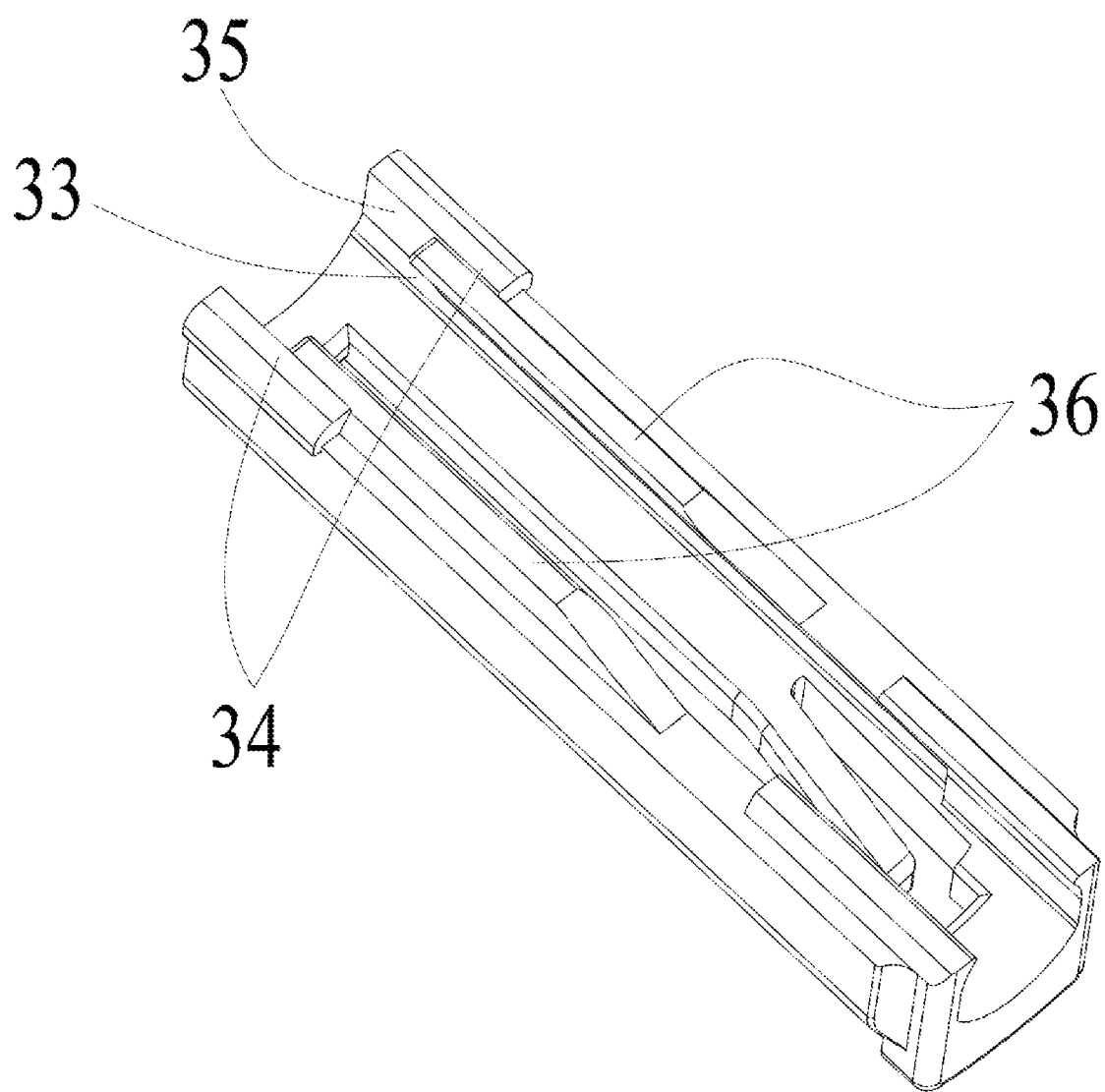
FIG. 3 is a schematic diagram of a built-in sliding sleeve according to the first embodiment of the present invention.
Figure 4:
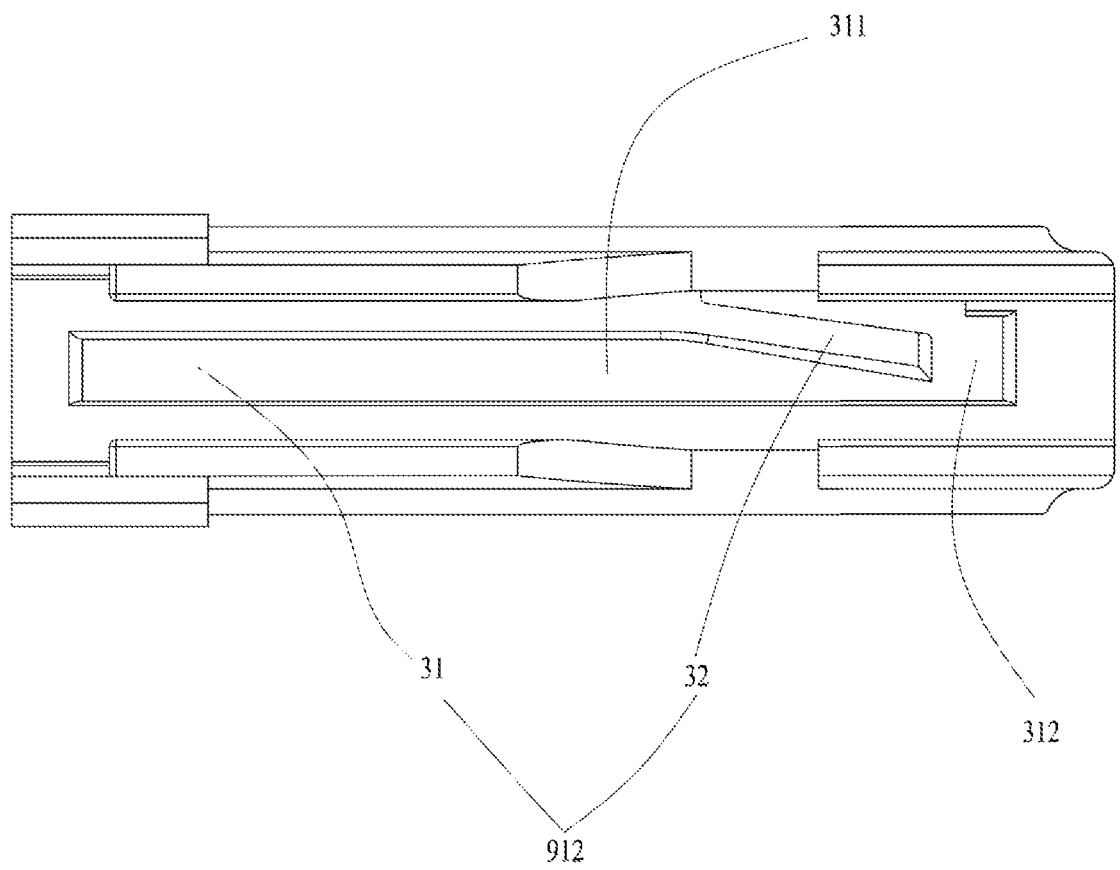
FIG. 4 is a bottom view of the built-in sliding sleeve according to the first embodiment of the present invention.
Figure 25:
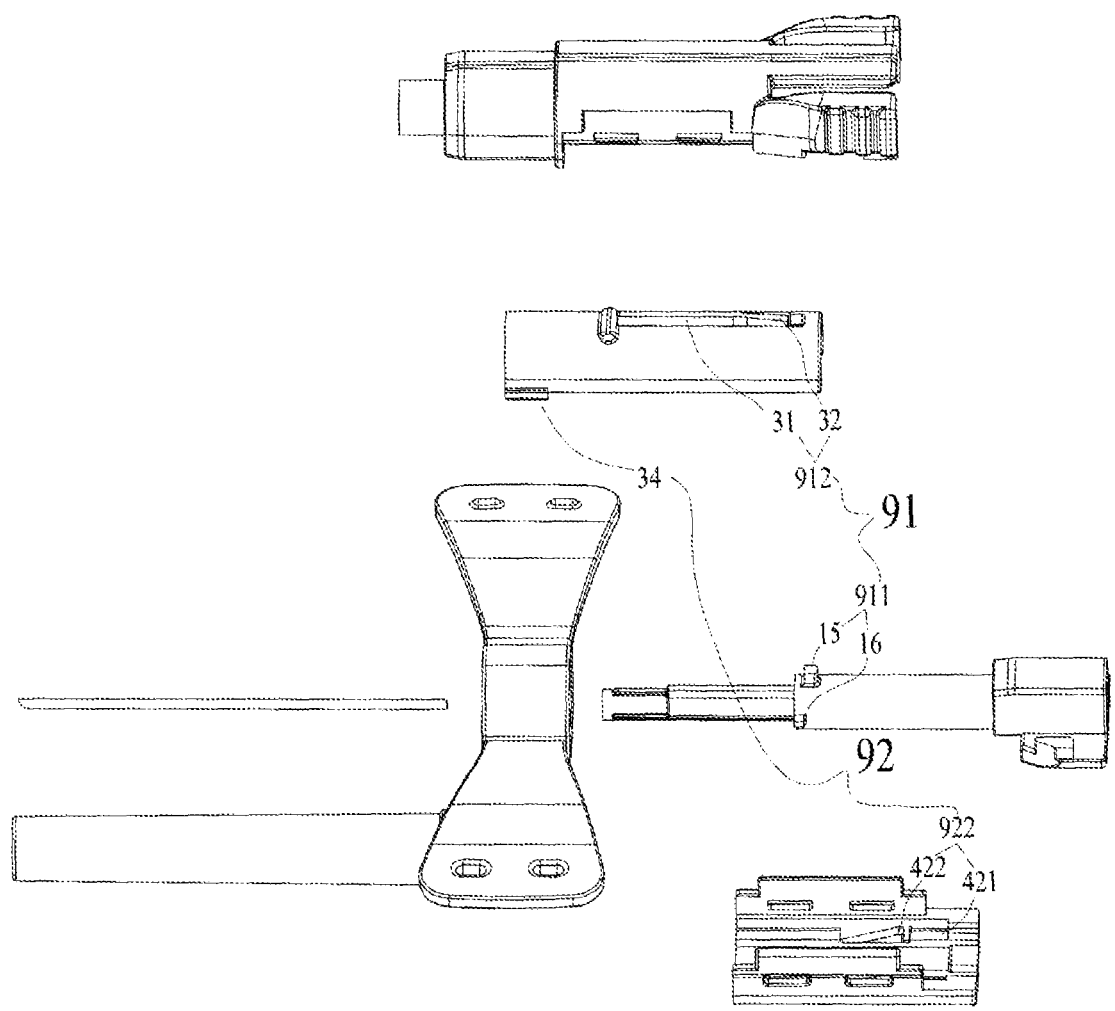
FIG. 25 is an exploded view of the auto-retractable blood collection needle of the present invention.

As shown in FIG. 25, the first locking mechanism 91 comprises a first positioning part 911 and a first locking part 912. As shown in FIG. 2, the first positioning part 911 is provided at a front end of an outer wall of the second tube 12 and comprises a built-in slider 15. As shown in FIGS. 3-4, the built-in sliding sleeve 3 is an elongate through block, and a cross section thereof is C-shaped. The first locking part 912 is provided on the inner wall of the built-in sliding sleeve 3 and comprises a groove 31 and a first elastic arm 32. The groove 31 is arranged along an axial direction and is located at a central line of the built-in sliding sleeve 3 of the width direction. The first elastic arm 32 is provided at a rear section of the groove 31. Specifically, a rear groove 311 gradually narrowing in width is formed at a rear end of the groove 31, and the rear groove 311 is bent and then extends to the front end of the groove 31 to form a fishhook-shaped through hole 312, so that the first elastic arm 32 is formed in the rear groove 311. The built-in slider 15 is limited to slide along the length of the groove 31. When the built-in slider 15 slides to the rear end of the groove 31, the built-in slider 15 pushes the first elastic arm 32 to generate an elasticity deformation to allow the built-in slider 15 to pass. When the built-in slider 15 reaches the fishhook-shaped through hole 312 at the rear end of the groove 31, the first elastic arm 32 recovers from the elastic deformation, and the built-in slider 15 is locked in the axial direction, so that the built-in slider is prevented from sliding reversely. Under the force of the spring 8, the second tube 12 drives the rear end of the built-in sliding sleeve 3 to slide out of the needle shield 4 when the second tube 12 is locked at the built-in sliding sleeve 3.

As shown in FIGS. 2 and 25, the first positioning part 911 further comprises two side sliders 16 which are symmetrically arranged at both sides of the built-in slider (in the drawing, one of the side sliders 16 is blocked). As shown in FIGS. 3-4, the first locking part 912 further comprises two first chutes 33 (in the drawing, one of the first chutes 33 is blocked). The two first chutes 33 are arranged along the axial direction and are symmetrically arranged on two inner sides of the built-in sliding sleeve 3. A bayonet 35 is provided on the front end of the built-in sliding sleeve 3, and the bayonet 35 has a width to allow the two side sliders 16 on the second tube 12 to fit with the bayonet, so that the two side sliders 16 engage with the two first chutes 33 from the front end of the built-in sliding sleeve 3. Therefore, the two side sliders 16 are limited to slide along lengths of the two first chutes 33, respectively. When the second tube 12 is mounted in the built-in sliding sleeve 3, the radial movement of the second tube 12 is restricted, so it is prevented from sliding out of the built-in sliding sleeve 3 in the radial direction. In this way, the second tube 12 and the built-in sliding sleeve 3 are stably assembled.

Figure 5:
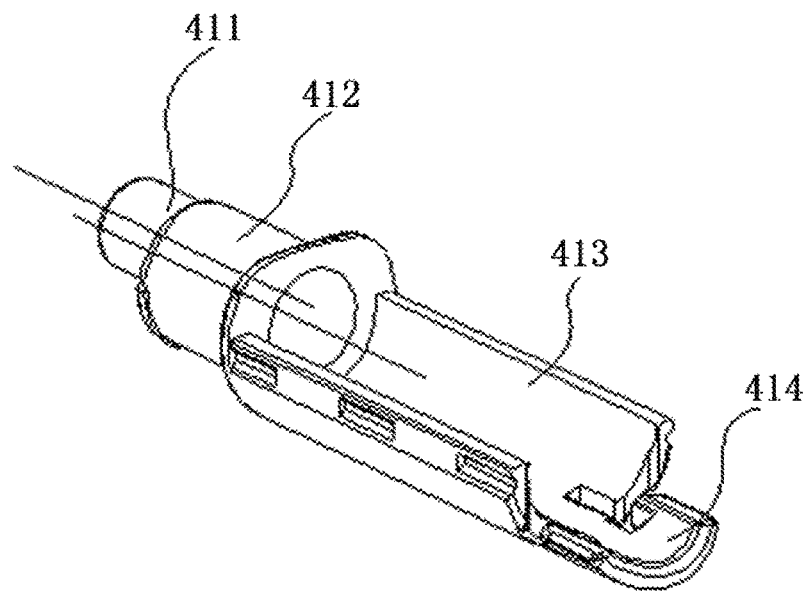
FIG. 5 is a schematic diagram of an upper shield according to the first embodiment of the present invention.
Figure 6:
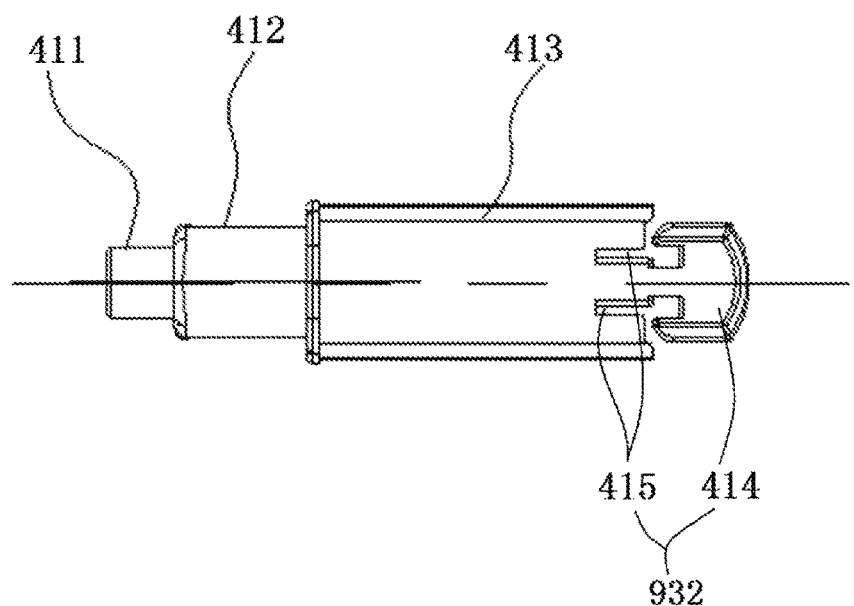
FIG. 6 is a bottom view of the upper shield according to the first embodiment of the present invention.
Figure 7:
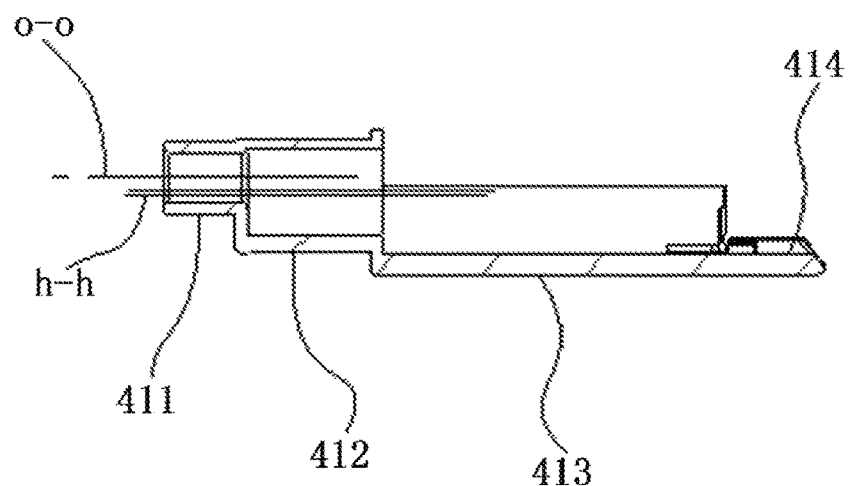
FIG. 7 is a cross section of the upper shield according to the first embodiment of the present invention.

As shown in FIGS. 1 and 5-9, the needle shield 4 is formed by fastening an upper shield 41 and a lower shield 42 together. The built-in sliding sleeve 3 is mounted in the upper shield 41. Two axial sections 36 of the built-in sliding sleeve are attached to an inner wall of the lower shield 42. As shown in FIGS. 5-7, the upper shield 41 comprises a third tube 411, a fourth tube 412 and a recess 413 having a C-shaped cross section which are connected in sequence. A diameter of the fourth tube 412 is larger than a diameter of the third tube 411, and a central axis o-o of the third tube 411 is parallel to a central axis h-h of the fourth tube 412. The first tube 11 of the tube holder 1 passes through the third tube 411 and the fourth tube 412, and a length of the bush 14 is same with that of the fourth tube 412. Specifically, a front end of the third tube 411 is open to allow the front end of the first tube 11 of the needle holder 1 to extend out; the front end of the spring 8 abuts on a step surface formed between the third tube 411 and the fourth tube 412; the built-in sliding sleeve 3 is provided in the fourth tube 412 and the recess 413, and a certain gap is provided between a front end surface of the built-in sliding sleeve 3 and the stepped surface formed between the third tube 411 and the fourth tube 412, so as to accommodate a part of the compressed spring 8, and the other part of the spring 8 is sheathed on the first tube 11 and located in the built-in sliding sleeve 3.

Figure 8:
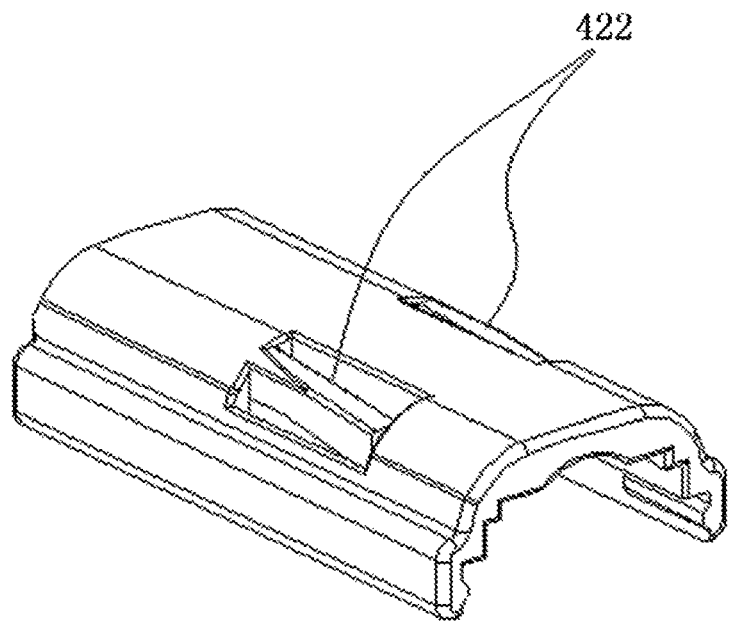
FIG. 8 is a schematic diagram of a lower shield according to the first embodiment of the present invention.
Figure 9:
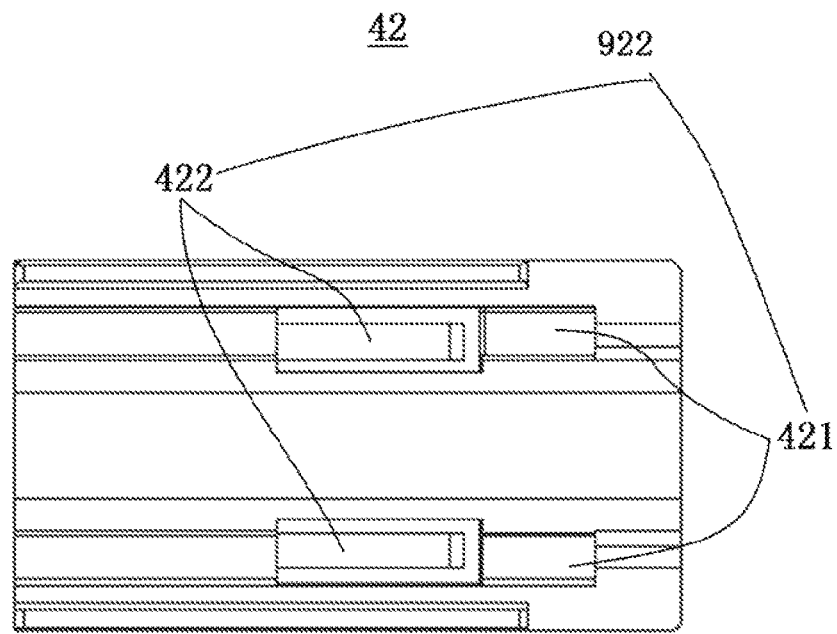
FIG. 9 is a top view of the lower shield according to the first embodiment of the present invention.

As shown in FIG. 25, the second locking mechanism 92 comprises a second positioning part and a second locking part 922. As shown in FIG. 3, the built-in sliding sleeve 3 is provided with a second positioning part comprising two protrusions 34 which are respectively arranged on two axial sections of the built-in sliding sleeve 3. As shown in FIGS. 8-9 and 25, the second locking part 922 is provided on the inner wall of the lower shield 42 and comprises two second chutes 421 and two second elastic arms 422. The two second chutes 421 are symmetrically arranged along an axial direction of the lower shield 42, and the two second elastic arms 422 are respectively disposed at rear sections of the two second chutes 421. The two protrusions 34 are respectively limited to slide along lengths of the two second chutes 421. When the two protrusions 34 slide towards rear ends of the two second chutes 421 along the two second chutes 421, respectively, the two second elastic arms 422 are pushed by the two protrusions 34 to generate an elastic deformation to allow the two protrusions 34 to pass. When the two protrusions 34 respectively reach the rear ends of the two second chutes 421, the two second elastic arms 422 recover from the elastic deformation, so that the two protrusions 34 are locked and are prevented from sliding reversely.

The third locking mechanism 93 comprises a third positioning part 931 and a third locking part 932. As shown in FIG. 2, the third positioning part 931 is provided on the holder tail 13 and comprises two claws 131 which are symmetrically arranged at an end surface of the holder tail 13 and perpendicular to the central axis of the second tube 12. As shown in FIGS. 5-7, the third locking part 932 is provided at the rear of the upper shield 41 and comprises a first sheet-like portion 414 and two bar-type holes 415. The first sheet-like portion 414 extends from the rear of the upper shield 41 in the axial direction, and the first sheet-like portion 414 can be turned in the radial direction. The two bar-type holes 415 are symmetrically provided on the first sheet-like portion 414. When the two claws 131 are respectively inserted into the two bar-type holes 415, the holder tail 13 is locked at the rear of the needle shield 4, and the spring 8 is in a compressed state. When the first sheet-like portion 414 is turned, the two claws 131 are unlocked from the two bar-type holes 415, respectively, so that the needle holder 13 is unlocked from the rear of the needle shield 4. Then, the second tube 12 of the needle holder 1 is pushed rearward under the force of the spring 8.

As shown in FIG. 1, the auto-retractable blood collection needle further comprises a wing assembly 5 which is sleeved on the fourth tube 412 of the needle shield 4. The wing assembly 5 has two wings which are symmetrically arranged and overlap with each other after they are folded. The wings 5 are made of elastic plastic. The surface of the wings 5 is provided with anti-slip structures such as granular protrusions or patterns to prevent the slipping. Such structure prevents the needle 2 from rotating in the blood vessel, thereby reducing the potential risk that the needle tip 21 damages the blood vessel.

The maximum vertical distance between the needle 2 and the outer wall of the lower shield 42 is approximately 1.4 mm. It should be noted that, in order to minimize the vertical distance between the central axis of the needle 2 and the bottom of the needle holder lto avoid a large inclination angle between the needle 2 and the needle holder of the needle 2, the built-in sliding sleeve 3 is designed to be an elongate through block, and the cross section thereof is C-shaped; the needle shield 4 is divided into the upper shield 41 and the lower shield 42 which are beneficial for molding production; the central axis of the first tube 11 is parallel to the central axis of the second tube 12, and the central axis of the first tube 11 is located between the central axis of the second tube 12 and the inner wall of the lower shield 42, so that the maximum vertical distance between the needle 2 and the outer wall of the lower shield 42 is reduced. During assembly, the built-in sliding sleeve 3 is installed in the upper shield 41, and the two axial sections of the built-in sliding sleeve 3 are attached to the inner wall of the lower shield 42. The first tube 11 installed with the needle 2 is close to the inner wall of the lower shield 42, so that the maximum vertical distance from the axis of the needle 2 to the outer wall of the lower shield 42 is less than or approximately equal to 1.5 mm.

In this embodiment, the auto-retractable blood collection needle is assembled with the following steps.

1) The needle 2 is mounted at the front end of the first tube 11 of the needle holder 1.

2) The second tube 12 of the needle holder 1 is inserted into the built-in sliding sleeve 3, and the holder tail 13 is located outside the rear of the built-in sliding sleeve 3.

3) The spring is sheathed on the first tube 11.

4) The assembled built-in sliding sleeve 3, the needle holder 1 and the spring 8 are placed into the upper shield 41. The front end of the spring 8 abuts against the stepped surface of the inner wall of the upper shield 41, and the rear of the spring 8 abuts against the front end surface of the second tube 12.

5) The needle shield 4 is formed by fastening the lower shield 42 and the upper shield 41 together. At this time, the third locking part 932 at the rear of the needle shield 4 is locked with the third positioning part 931 of the holder tail 13 to lock the holder tail 13 to the rear of the needle shield 4; the spring 8 is in a compressed state; and the built-in sliding sleeve 3 is locked by the holder tail 13 of the needle holder 1; the first locking mechanism 91 and the second locking mechanism 92 both are not in a locking state.

6) The wing assembly 5 is sheathed on the peripheral surface of the needle shield 4.

The operation method of the blood collection needle of this embodiment is same with that of conventional blood collection needles. However, when pulling back the needle, one hand is required to turn the first sheet-like portion 414 to allow the two claws 131 to respectively unlock from the two bar-type holes 415, so that the holder tail 13 is unlocked from the rear of the needle shield 4. Under the force of the spring 8, the second tube 12 of the needle holder 1 is pushed from the built-in sliding sleeve 3 to the first elastic arm 32 of the first locking part 912, so that the second tube is locked, and the built-in sliding sleeve 3 is pushed from the needle shield 4 to the locking position to be locked. At this time, both the needle holder 1 and the built-in sliding sleeve 3 are not allowed to move back and forth, and the needle 2 is fully retracted into the needle shield 4, so that the needle 2 is pulled out of the patient.

Example 2

Figure 10:
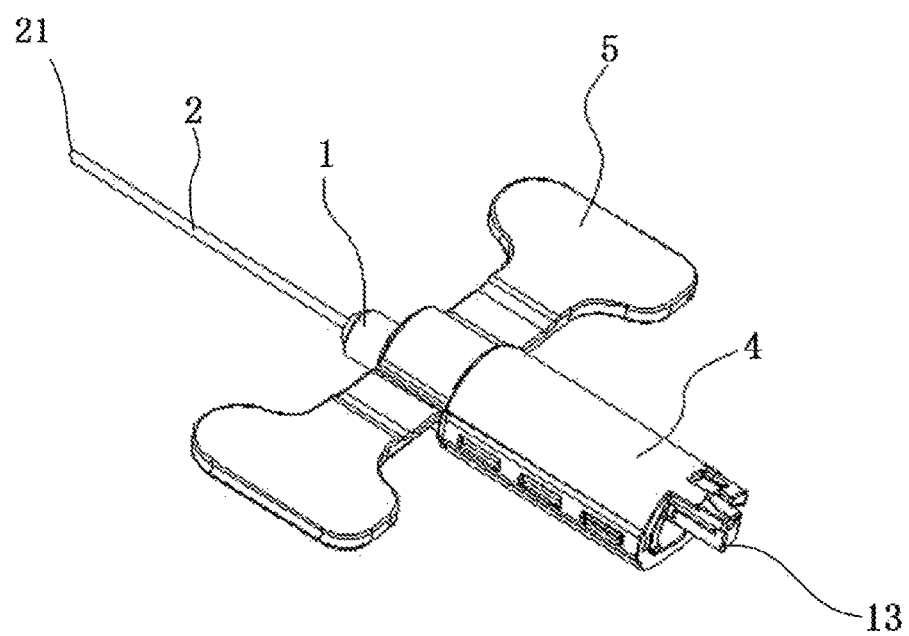
FIG. 10 is a schematic diagram of the auto-retractable blood collection needle according to a second embodiment of the present invention.
Figure 11:
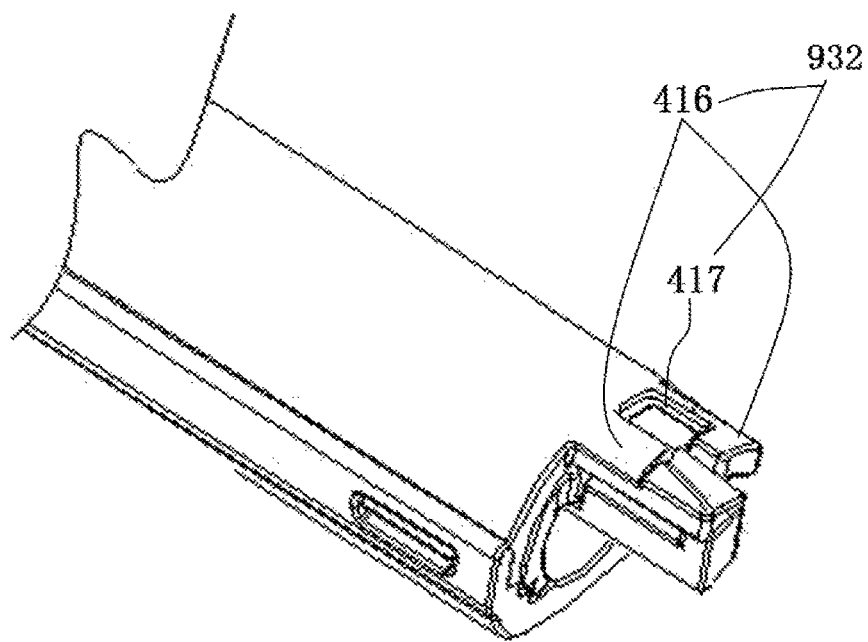
FIG. 11 is an enlarged view of a rear of the auto-retractable blood collection needle according to the second embodiment of the present invention.
Figure 12:
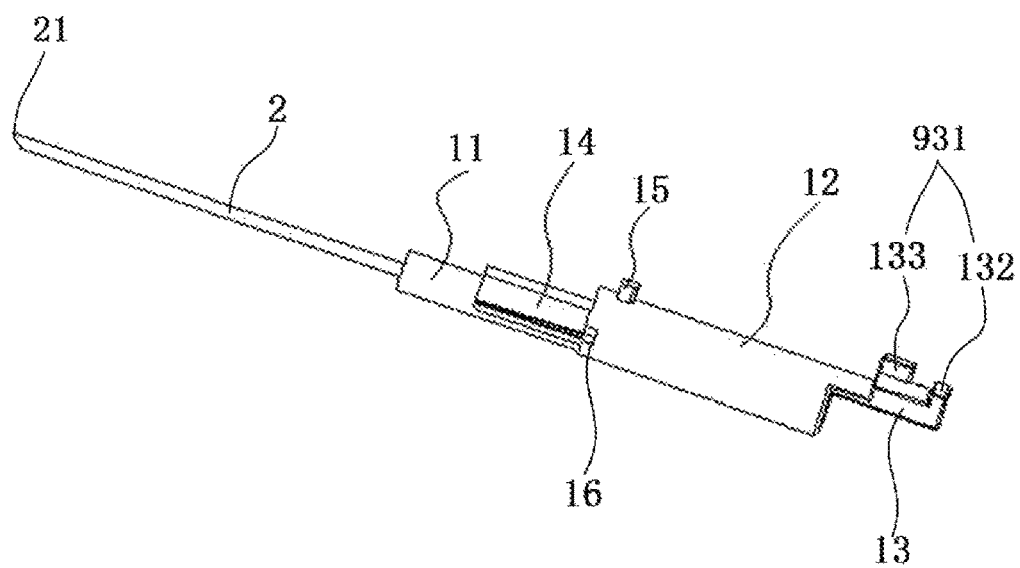
FIG. 12 is a schematic diagram of the needle holder according to the second embodiment of the present invention.
Figure 13:
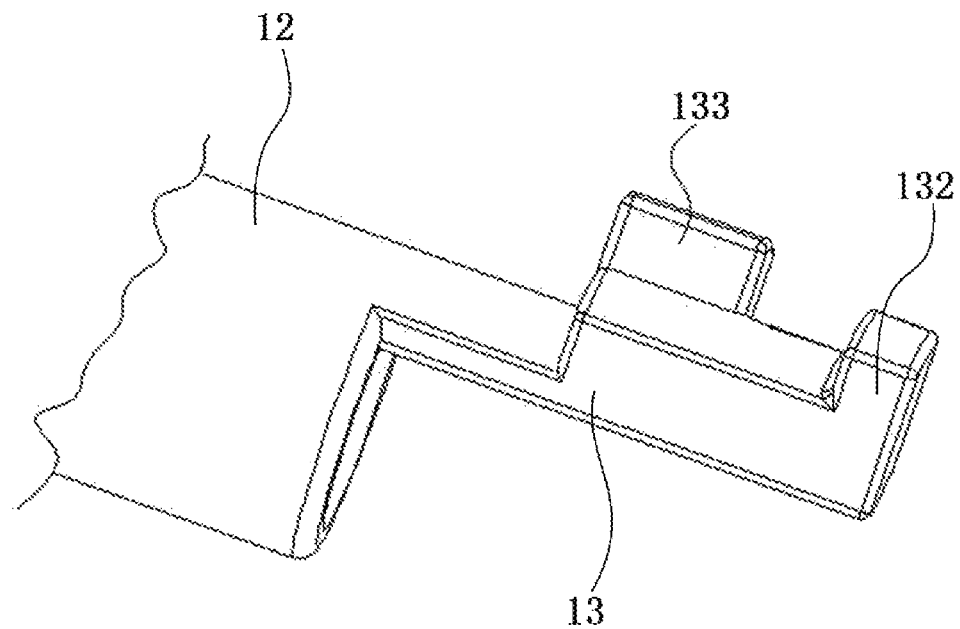
FIG. 13 is an enlarged view of a rear of the needle holder according to the second embodiment of the present invention.

As shown in FIGS. 10-13, this embodiment is same with Example 1 except for the third locking mechanism 93. In this embodiment, the third locking mechanism 93 comprises a third positioning part 931 and a third locking part 932. As shown in FIGS. 10-11, the third locking part 932 is provided at the rear of the upper shield 41 and comprises two second sheet-like portions 416 and a first engaging portion 417. The two second sheet-like portions 416 extend from the rear of the needle shield 4 in the axial direction and are adjacent to each other, and the first engaging portion 417 is arranged on one of the two second sheet-like portions 416. The third positioning part 931 comprises a first pressing portion 132 and a first protrusion 133. The first pressing portion 132 extends from the rear of the holder tail 13 in the axial direction, and the first protrusion 133 is provided on an outer wall of the first pressing portion 132. When the first protrusion 133 is inserted into the first engaging portion 417, the holder tail 13 is locked at the rear of the needle shield 4, and the spring 8 is in a compressed state. When the first pressing portion 132 is pressed, the first protrusion 133 is unlocked from the first engaging portion 417, so that the holder tail 13 is unlocked from the rear of the needle shield 4, and the second tube 12 is pushed rearward.

The first pressing portion 132 is provided with a triangular block which has an inclined surface P to facilitate the pressing. Moreover, a step of an edge of the triangular block is locked with the first protrusion 133, so the first protrusion is not unlocked from the first engaging portion when the triangular block is accidently pressed.

In this embodiment, the maximum vertical distance between the needle 2 and the peripheral surface of the lower shield 42 is 1.3 mm.

The auto-retractable blood collection needle of this embodiment is assembled according to the assembling steps in Example 1.

The operation method of the auto-retractable blood collection needle of this embodiment is same with that of conventional blood collection needles. However, when pulling back the needle, one hand is required to press the first pressing portion 132 to allow the first protrusion 133 to unlock from the first engaging portion 417, so that the holder tail 13 is unlocked from the rear of the needle shield 4. Under the force of the spring 8, the second tube 12 of the needle holder 1 is pushed from the built-in sliding sleeve 3 to the first elastic arm 32 of the first locking part 912, so that the second tube is locked, and the built-in sliding sleeve 3 is pushed from the needle shield 4 to the second elastic arms 422 of the second locking part 922, so that the built-in sliding sleeve is locked. At this time, both the needle holder 1 and the built-in sliding sleeve 3 are not allowed to move back and forth, and the needle 2 is fully retracted into the needle shield 4, so that the needle 2 is pulled out of the patient.

Example 3

Figure 14:
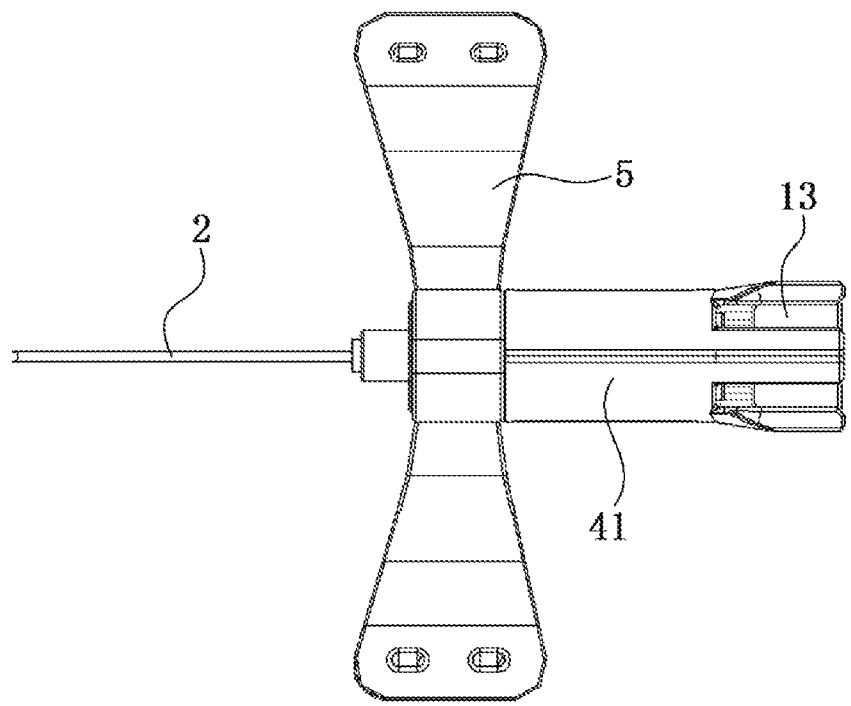
FIG. 14 is a top view of the auto-retractable blood collection needle according to a third embodiment of the present invention.
Figure 15:
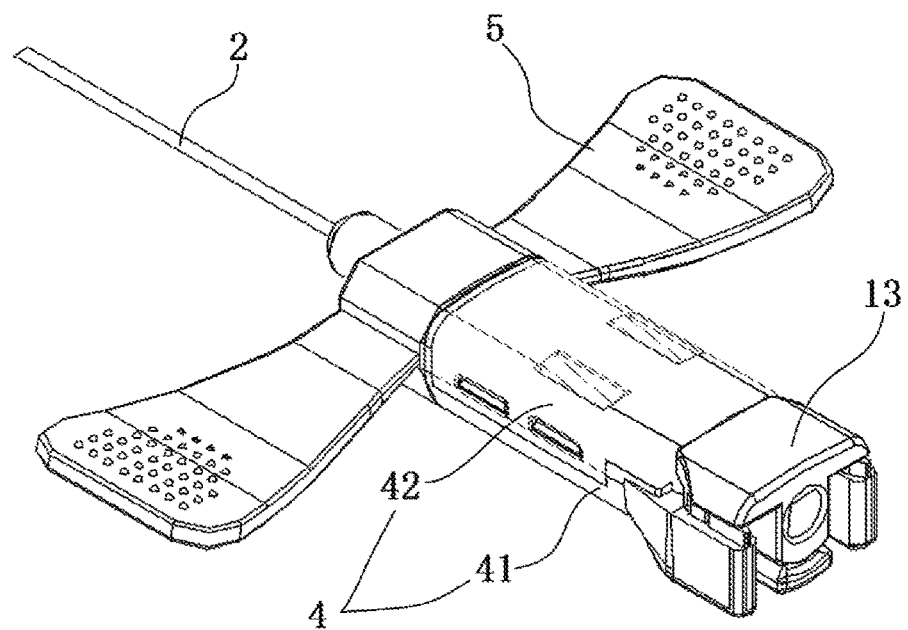
FIG. 15 is a schematic diagram of the auto-retractable blood collection needle according to the third embodiment of the present invention.
Figure 16:
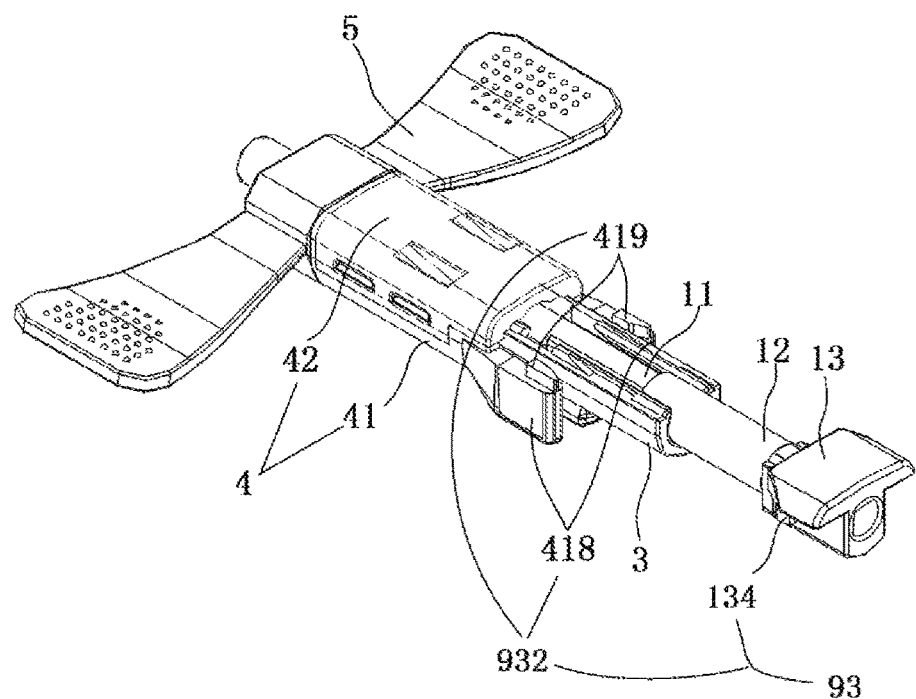
FIG. 16 is a schematic diagram of the auto-retractable blood collection needle after used according the third embodiment of the present invention, in which the blood collection needle is in an open state.

As shown in FIGS. 14-16, this embodiment is similar to Examples 1 and 2 except for the third locking mechanism 93. The third locking mechanism 93 comprises a third positioning part 931 and a third locking part 932. The third positioning part 931 comprises two second protrusions 134 (one of the two second protrusions 134 is blocked in the drawing). The two second protrusions are respectively arranged on both sides of the holder tail 13. The third locking part 932 is provided at the rear of the upper shield 41 and comprises two second pressing portions 418 and two second engaging portions 419. The two second pressing portions 418 extend rearward from two sides of the rear of the needle shield 4, and the two second pressing portions 418 can be pressed towards each other. The two second engaging portions 419 are respectively provided on the two second pressing portions 418. When assembling, the holder tail 13 is pushed to slide forward, and when the two second protrusions 134 are respectively engaged in the two second engaging portions 419, the holder tail 13 is locked at the rear of the needle shield 4, and the spring 8 is a compressed state. When the second pressing portions 418 on the two sides of the rear of the needle shield 4 are pressed towards each other, the two second protrusions 134 are unlocked from the two second engaging portions 419, respectively, so that the holder tail 13 is unlocked from the rear of the needle shield 4. Then, under the force of the spring 8, the second tube 12 of the needle holder 1 is pushed backward.

The front ends of the two second protrusions 134 are designed to be inclined, so that the two second protrusions 134 can be respectively stuck into the two second engaging portions 419.

In this embodiment, the maximum vertical distance between the needle 2 and the peripheral surface of the lower shield 42 is approximately 1.2 mm.

The auto-retractable blood collection needle of this embodiment is assembled according to the assembling steps in Example 1.

The operation method of the auto-retractable blood collection needle of this embodiment is same with that of conventional blood collection needles. However, when pulling back the needle, one hand is required to press the needle shield 4, and the other hand presses the second pressing portions 418 of the two sides towards each other to allow the second protrusions 134 to unlock from the second engaging portions 419, so that the holder tail 13 is unlocked from the rear of the needle shield 4. Under the force of the spring 8, the second tube 12 of the needle holder 1 is pushed from the built-in sliding sleeve 3 to the first elastic arm 32 of the first locking part 912, so that the second tube is locked, and the built-in sliding sleeve 3 is pushed from the needle shield 4 to the second elastic arms 422 of the second locking part 922, so that the built-in sliding sleeve 3 is locked. As shown in FIG. 15, at this time, both the needle holder 1 and the built-in sliding sleeve 3 are not allowed to move back and forth, and the needle 2 is fully retracted into the needle shield 4, so that the needle 2 is pulled out of the patient.

Example 4

Figure 17:
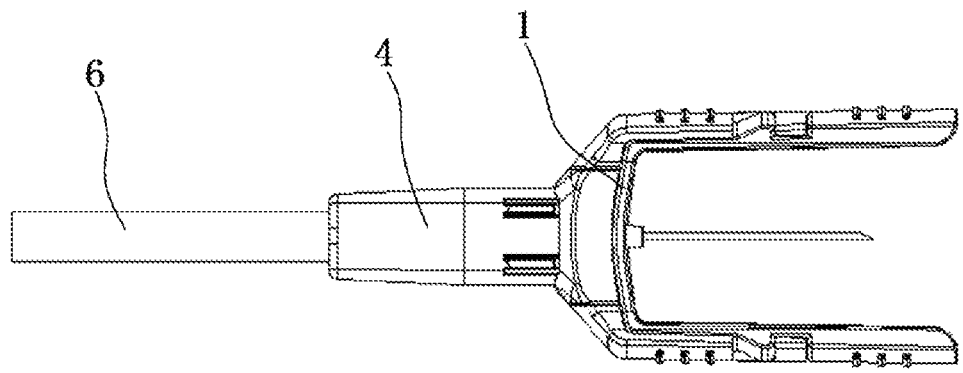
FIG. 17 is a schematic diagram of the auto-retractable blood collection needle according to a fourth embodiment of the present invention.

As shown in FIG. 17, a pen-type blood collection needle is illustrated in this embodiment. This embodiment and Examples 1-3 are different in the rear structure of the needle shield 4, the holder tail 13 and the third locking mechanism 93. The third locking mechanism 93 comprises a third positioning part 931 and a third locking part 932.

Figure 18:
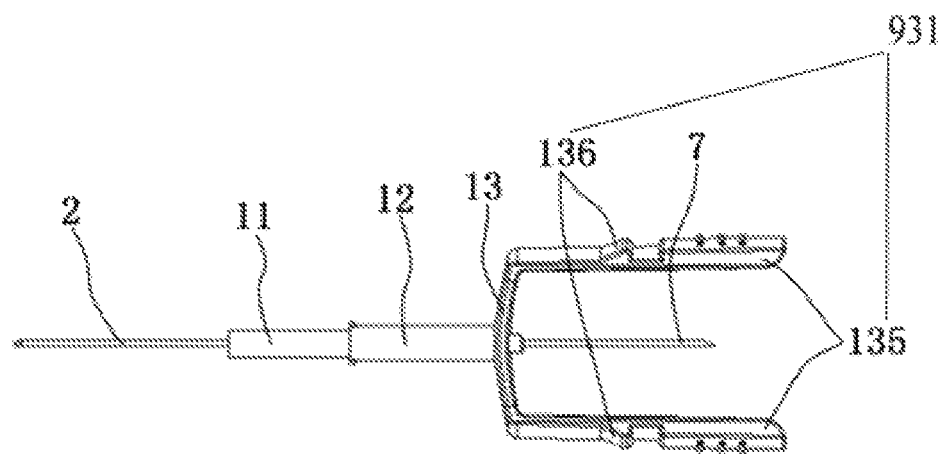
FIG. 18 is a top view of the needle holder of the auto-retractable blood collection needle according to the fourth embodiment of the present invention.
Figure 19:
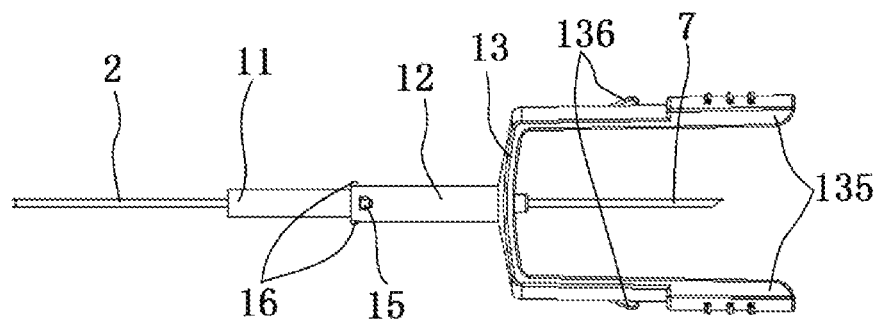
FIG. 19 is a bottom view of the needle holder of the auto-retractable blood collection needle according to the fourth embodiment of the present invention.

As shown in FIGS. 18-19, the holder tail 13 of the needle holder 1 is approximately U-shaped and opens backward. The holder tail 13 is provided with a third positioning part 931 comprising two third pressing portions 135 and two third protrusions 136. The two third pressing portions 135 are two side walls of a rear section of the holder tail 13, and the two third protrusions 136 are respectively disposed on the two side walls of a front section of the holder tail 13. In this embodiment, the first tube 11 and the second tube 12 are coaxially arranged, and the holder tail 13 is provided with an additional needle 7 having the same axis with the needle 2, which is different from Examples 1-3.

Figure 20:
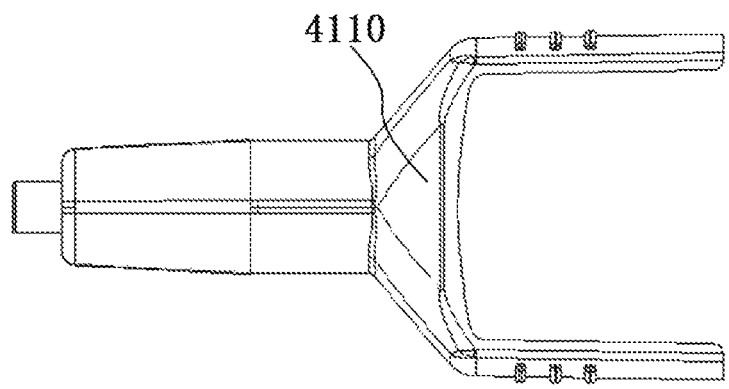
FIG. 20 is a top view of the upper shield of the auto-retractable blood collection needle according to the fourth embodiment of the present invention.
Figure 21:
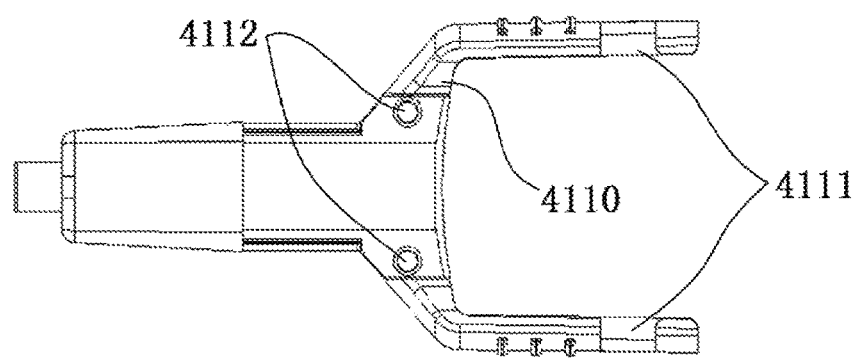
FIG. 21 is a bottom view of the upper shield of the auto-retractable blood collection needle according to the fourth embodiment of the present invention.
Figure 22:
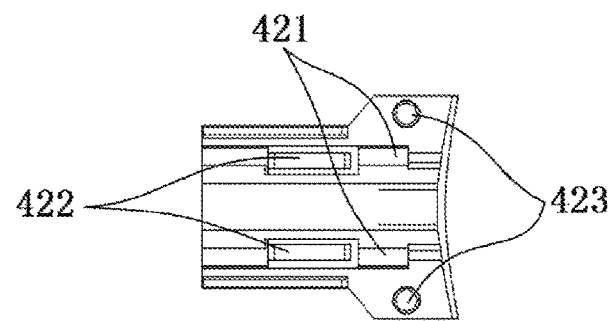
FIG. 22 is a top view of the lower shield of the auto-retractable blood collection needle according to the fourth embodiment of the present invention.
Figure 23:
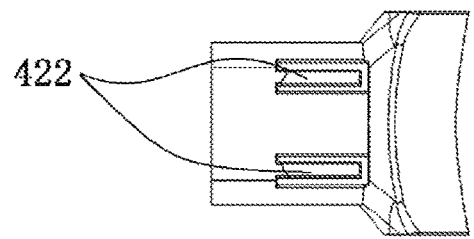
FIG. 23 is a bottom view of the lower shield of the auto-retractable blood collection needle according to the fourth embodiment of the present invention.

As shown in FIGS. 20-21, the rear of the upper shield 41 extends backward to form a handheld portion 4110 which is approximately U-shaped and opens rearward. The third locking part 932 is provided on the handheld portion 4110 and comprises two third engaging portions 4111 which are respectively provided on two side walls of the handheld portion 4110. The structure of the lower shield 42 is shown in FIGS. 22-23. Circular parts in the drawing are circular protrusions 423 which are configured to engage with the circular grooves 4112 of the upper shield 41 to fasten the upper shield 41 and the lower shield 42 together.

When the front section of the holder tail 13 is arranged in side and locked with the handheld portion 4110, and the rear section of the holder tail 13 is located behind the rear of the handheld portion 4110, and specifically, when the two third protrusions 136 respectively engage with the two third engaging portions 4111, and the two pressing portions 135 are respectively located at rears of the two side walls of the handheld portion 4110, the hold tail 13 is locked at the rear of the needle shield 4, and the spring 8 is in a compressed state. When the two third pressing portions 135 are pressed towards each other, the two third protrusions 136 are unlocked from the two third engaging portions 4111, respectively, so that the holder tail 13 is unlocked from the rear of the needle shield 4. Then, under the force of the spring 8, the second tube 12 of the needle holder 1 is pushed to move rearward.

The auto-retractable blood collection needle of this embodiment is assembled according to the assembling steps in Example 1, and a sheath 6 can be sheathed on the needle 2.

Figure 24:
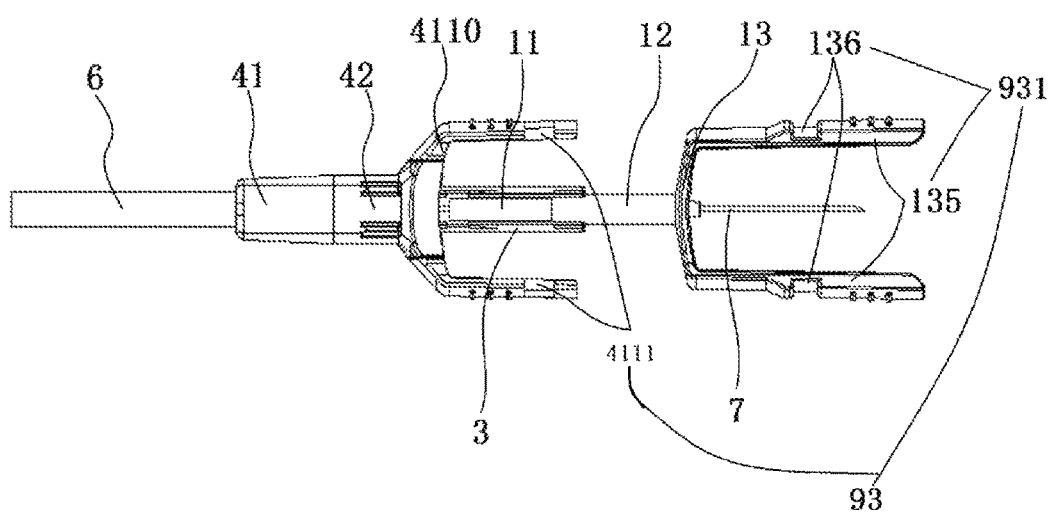
FIG. 24 is a schematic diagram of the auto-retractable blood collection needle after used according to the fourth embodiment of the present invention, in which the auto-retractable blood collection needle is in an open state.

The operation method of the auto-retractable blood collection needle of this embodiment is same with that of conventional blood collection needles. However, when pulling back the needle, one hand is required to press the handheld portion 4110 of the needle shield 4, and the other hand presses the two third pressing portions 135 of the two sides towards each other to allow the third protrusions 136 to unlock from the two third engaging portions 4111, so that the holder tail 13 is unlocked from the rear of the needle shield 4. Under the force of the spring 8, the second tube 12 of the needle holder 1 is pushed from the built-in sliding sleeve 3 to the first elastic arm 32 of the first locking part 912, so that the second tube is locked, and then the built-in sliding sleeve 3 is pushed from the needle shield 4 to the second elastic arms 422 of the second locking part 922, so that the built-in sliding sleeve is locked. As shown in FIG. 24, at this time, both the needle holder 1 and the built-in sliding sleeve 3 are not allowed to move back and forth, and the needle 2 is fully retracted into the needle shield 4, so that the needle 2 is pulled out of the patient.

In addition, in this embodiment, the spring 8 can be removed from the pen-type blood collection needle. When pulling out the needle, one hand is required to press the handheld portion 4110 of the needle shield 4, and the other hand presses the two third pressing portions 135 of the two sides towards each other to allow the two third protrusions 136 to unlock from the two third engaging portions 4111, and then the needle holder 1 is pulled rearward, so that the second tube 12 of the needle holder 1 is pulled from the built-in sliding sleeve 3 to the first elastic arm 32 of the first locking part 912, so that the second tube is locked, and then the built-in sliding sleeve 3 is pulled from the needle shield 4 to the second elastic arms 422 of the second locking part 922, so that the built-in sliding sleeve is locked. At this time, both the needle holder 1 and the built-in sliding sleeve 3 are not allowed to move forward and backward, and the needle 2 is fully retracted into the needle shield 4, so that the needle 2 is pulled out of the patient.

It should be noted that in the above embodiments, configurations of the positioning part and the locking part can be interchanged, that is, the positioning part can also be concave, and the locking part can also be convex if the locking can be realized by the concave and convex configurations.

The above are only preferred embodiments of the present invention. It should be noted that, improvements and modifications made by those skilled in the art without departing from the principles of the present invention shall fall within the scope of the present invention.

I claim:

1. An auto-retractable safety blood collection needle, comprising:
    a needle holder comprising a first tube, a second tube and a holder tail connected in sequence;
    a needle;
    a built-in sliding sleeve which is elongated and has a C-shaped cross section;
    a needle shield which is hollow and elongated; and
    a spring;
    wherein a diameter of the second tube is larger than a diameter of the first tube; a rear of the needle is mounted in the first tube; the first tube and the second tube both are installed in the built-in sliding sleeve; a built-in slider is provided on a peripheral surface of the second tube, and the second tube matches with the built-in slider to allow the second tube to slide back and forth; a holder tail of the needle holder is located outside a rear of the built-in sliding sleeve which is mounted in the needle shield and is capable of sliding back and forth; the holder tail is allowed to be locked at or unlocked from a rear of the needle shield; the spring is sheathed on the first tube; a front end of the spring abuts against an inner wall of the needle shield, and a rear of the spring abuts against a front end of the second tube;

a first locking mechanism is provided between the needle holder and the built-in sliding sleeve and is configured for locking the second tube with the built-in sliding sleeve; a second locking mechanism is provided between the built-in sliding sleeve and the needle shield and is configured for locking the built-in sliding sleeve with the needle shield; a third locking mechanism is provided between the holder tail and the needle shield and is configured for locking the holder tail with the needle shield;

when the holder tail is locked at the rear of the needle shield, the spring is in a compressed state, and a front end and the rear of the built-in sliding sleeve are respectively limited by the inner wall of the needle shield and the holder tail; when the holder tail is unlocked from the rear of the needle shield, the spring forces the second tube to slide rearward to a locking position of the first locking mechanism, so that the second tube is locked at the built-in sliding sleeve; the needle holder keeps sliding rearward, and the built-in sliding sleeve is driven to slide rearward to a locking position of the second locking mechanism, so that the built-in sliding sleeve is locked at the needle shield; at this time, the needle is fully covered by the needle shield, and a needle tip is not exposed.

2. The auto-retractable safety blood collection needle of claim 1, wherein the first locking mechanism comprises a first positioning part arranged on an outer wall of the second tube and a first locking part arranged on an inner wall of the built-in sliding sleeve; when the second tube slides to a locking position of the first locking part, the first positioning part is locked by the first locking part, so that the second tube is prevented from sliding out of the built-in sliding sleeve.

3. The auto-retractable safety blood collection needle of claim 2, where in the first positioning part comprises the built-in slider; the first locking part comprises a groove arranged along an axial direction of the built-in sliding sleeve and a first elastic arm arranged at a rear section of the groove; the built-in slider is limited to slide along a length of the groove; when the built-in slider slides to a rear end of the groove, the built-in slider pushes the first elastic arm to generate an elastic deformation to allow the built-in slider to pass; when the built-in slider reaches the rear end of the groove, the first elastic arm recovers from the elastic deformation, so that the built-in slider is locked and is prevented from sliding reversely.

4. The auto-retractable safety blood collection needle of claim 3, wherein the first positioning part further comprises two side sliders which are symmetrically arranged on both sides of the built-in slider; the first locking part further comprises two first chutes which are arranged along the axial direction of the built-in sliding sleeve and are symmetrically arranged on two inner sides of the built-in sliding sleeve; the two side sliders are limited to slide along lengths of the two first chutes, respectively, so that the two side sliders are prevented from sliding out of the built-in sliding sleeve in a radial direction.

5. The auto-retractable safety blood collection needle of claim 1, wherein the second locking mechanism comprises a second positioning part which is arranged on the built-in sliding sleeve and a second locking part which is provided on the inner wall of the needle shield; when the built-in sliding sleeve slides to a locking position of the second locking part, the second positioning part is locked by the second locking part, so that the built-in sliding sleeve is prevented from sliding out of the needle shield.

6. The auto-retractable safety blood collection needle of claim 5, wherein the second positioning part comprises two protrusions respectively arranged on two axial sections of the built-in sliding sleeve; the second locking part comprises two second chutes and two second elastic arms which are respectively arranged at rear sections of the two second chutes, and the two protrusions are respectively limited to slide along lengths of the two second chutes; when the two protrusions slide towards rear ends of the two second chutes along the two second chutes, respectively, the two second elastic arms are pushed by the two protrusions to generate an elastic deformation to allow the two protrusions to pass; when the two protrusions respectively reach the rear ends of the two second chutes, the two second elastic arms recover from the elastic deformation, so that the two protrusions are locked and are prevented from sliding reversely.

7. The auto-retractable safety blood collection needle of claim 1, wherein the third locking mechanism comprises a third positioning part arranged at the holder tail and a third locking part arranged on the rear of the needle shield; when the third positioning part is locked at the third locking part, the holder tail is locked at the rear of the needle shield, and the spring is in a compressed state; when the third positioning part is unlocked from the third locking part, a force of the spring pushes the second tube to allow the needle holder to move rearward.

8. The auto-retractable safety blood collection needle of claim 7, wherein the third positioning part comprises two claws which are symmetrically arranged at a rear end surface of the holder tail and perpendicular to a central axis of the second tube; the third locking part comprises a first sheet-like portion and two bar-type holes; the first sheet-like portion extends from the rear of the needle shield along the axial direction, and is elastically movable in a radial direction of the needle shield; the two bar-type holes are symmetrically provided on the first sheet-like portion; the first sheet-like portion is operated to respectively insert the two claws into the two bar-type holes, or unlock the two claws from the two bar-type holes.

9. The auto-retractable safety blood collection needle of claim 7, wherein the third positioning part comprises a first pressing portion and a first protrusion; the first pressing portion extends from a rear of the holder tail along an axial direction and is pressed along a radial direction; the first protrusion is provided on an outer wall of the first pressing portion; the third locking part comprises two second sheet-like portions and a first engaging portion; the two second sheet-like portions extend from the rear of the needle shield along the axial direction and are adjacent to each other, and the first engaging portion is arranged on one of the two second sheet-like portions; the first pressing portion is pressed to insert the first protrusion into the first engaging portion, or unlock the first protrusion from the first engaging portion.

10. The auto-retractable safety blood collection needle of claim 7, wherein the third positioning part comprises two second protrusions which are respectively arranged on both sides of the holder tail; the third locking part comprises two second pressing portions and two second engaging portions; the two second pressing portions respectively extend rearward from two sides of the rear of the needle shield, and the two second pressing portions are pressed towards each other;

the two second engaging portions are respectively provided on the two second pressing portions; when the two second pressing portions are respectively inserted in the two second engaging portions, the holder tail is locked at the rear of the needle shield; and when the second pressing portions on two sides of the rear of the needle shield are pressed towards each other, the two second protrusions are unlocked from the two second engaging portions, respectively.

11. The auto-retractable safety blood collection needle of claim 7, wherein the rear of the needle shield extends rearward to form a handheld portion; the handheld portion and the holder tail both are approximately U-shaped and open rearward; a front section of the holder tail is located inside and locked with the handheld portion; a rear section of the holder tail is located behind a rear of the handheld portion; the third positioning part comprises two third pressing portions and two third protrusions; the two third pressing portions are two side walls of the rear section of the holder tail, respectively; the third locking part comprises two third engaging portions which are respectively provided on two side walls of the handheld portion; when the two third protrusions respectively engage with the two third engaging portions, the two third pressing portions are respectively located behind rears of two side walls of the handheld portion; and when the two third pressing portions located at two sides of the rear section of the holder tail are pressed towards each other, the two third protrusions are respectively unlocked from the two third engaging portions.

12. The auto-retractable safety blood collection needle of claim 11, wherein the first tube and the second tube are coaxially arranged.

13. The auto-retractable safety blood collection needle of claim 1, further comprising a wing assembly which is sheathed on the needle shield, wherein the wing assembly has two wings which are symmetrically arranged and overlap with each other after folded.

14. The auto-retractable safety blood collection needle of claim 1, wherein the needle shield is formed by fastening an upper shield and a lower shield together; the built-in sliding sleeve is installed in the upper shield; and two axial sections of the built-in sliding sleeve are attached on an inner wall of the lower shield.

15. The auto-retractable safety blood collection needle of claim 1, wherein a maximum vertical distance between the needle and an outer wall of a lower shield is less than or equal to 1.5 mm.

16. The auto-retractable safety blood collection needle of claim 15, wherein a central axis of the first tube is parallel to a central axis of the second tube, and the central axis of the first tube is located between the central axis of the second tube and the inner wall of the lower shield.

* * * * *